(12) United States Patent
Stad et al.

(10) Patent No.: US 8,709,094 B2
(45) Date of Patent: Apr. 29, 2014

(54) ANTI-ADHESION SHEET

(75) Inventors: Shawn Stad, Fall River, MA (US); Michael J O'Neil, West Barnstable, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 328 days.

(21) Appl. No.: 11/426,464

(22) Filed: Jun. 26, 2006

(65) Prior Publication Data

US 2007/0297987 A1 Dec. 27, 2007

(51) Int. Cl.
*A61F 2/02* (2006.01)

(52) U.S. Cl.
USPC ............. 623/23.72; 623/1.46; 623/16.11; 623/17.12; 623/23.76

(58) Field of Classification Search
USPC ............ 604/358, 362; 623/1.13, 1.46, 23.74, 623/23.76; 428/195, 323, 327, 480, 40.1, 428/41.7, 42.3, 198, 202; 442/43, 45–47
See application file for complete search history.

(56) References Cited

U.S. PATENT DOCUMENTS

| | | | |
|---|---|---|---|
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 5,071,823 A * | 12/1991 | Matsushita et al. | 503/227 |
| 5,464,929 A | 11/1995 | Bezwada | |
| 5,593,441 A | 1/1997 | Lichtenstein | |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |
| 5,620,698 A | 4/1997 | Bezwada | |
| 5,645,850 A | 7/1997 | Bezwada | |
| 5,648,088 A | 7/1997 | Bezwada | |
| 5,698,213 A | 12/1997 | Jamiolkowski | |
| 5,700,583 A | 12/1997 | Jamiolkowski | |
| 5,792,128 A * | 8/1998 | DeBusk | 604/362 |
| 5,859,150 A | 1/1999 | Jamiolkowski | |
| 5,891,824 A * | 4/1999 | Simpson et al. | 503/227 |
| 6,179,840 B1 | 1/2001 | Bowman | |
| 6,364,884 B1 | 4/2002 | Bowman | |
| 6,402,766 B2 | 6/2002 | Bowman | |
| 6,423,073 B2 | 7/2002 | Bowman | |
| 6,436,110 B2 | 8/2002 | Bowman | |
| 6,468,928 B2 * | 10/2002 | Eysel et al. | 442/45 |
| 6,475,219 B1 | 11/2002 | Shelokov | |
| 6,482,491 B1 * | 11/2002 | Samuelsen et al. | 428/40.1 |
| 6,497,707 B1 | 12/2002 | Bowman | |
| 6,869,938 B1 | 3/2005 | Schwartz | |
| 7,758,654 B2 * | 7/2010 | Hoganson | 623/23.74 |
| 7,767,222 B2 * | 8/2010 | Calhoun et al. | 424/426 |
| 2002/0052628 A1 | 5/2002 | Bowman | |
| 2002/0095157 A1 | 7/2002 | Bowman | |
| 2002/0095205 A1 * | 7/2002 | Edwin et al. | 623/1.13 |
| 2002/0169465 A1 | 11/2002 | Bowman | |
| 2004/0018228 A1 | 1/2004 | Fischell | |
| 2004/0138664 A1 | 7/2004 | Bowman | |
| 2005/0192600 A1 | 9/2005 | Nicolo et al. | |
| 2005/0192699 A1 | 9/2005 | Lin et al. | |
| 2005/0228491 A1 * | 10/2005 | Snyder et al. | 623/1.46 |

OTHER PUBLICATIONS

Cohn and Younes, Biodegradable PEO/PLA, Journal of Biomaterials Research, 1988, pp. 993-1009, vol. 22.
Cohn, Biomaterials Reserach Laboratory, Casali Institute of Applied Chemistry, The Hebrew University of Jerusalem, Polymer Preprints (ACS Division of Polymer Chemistry), 1989, p. 498, vol. 30(1).
Allcock, Polyphosphazenes, The Encyclopedia of Polymer Science, 1988, pp. 31-41, vol. 13, Wiley Intersciences, John Wiley & Sons.
Vandorpe, et al., Biodegradable polyphosphazenes for Bioemdical Applications, Handbook of Biodegradable Polymers, 1997, pp. 161-182, edited by Domb, et al, Hardwood Academic Press.
Heller, Poly (Ortho Esters), Handbook of Biodegradable Polymers, 1997, pp. 99-118, edited by Domb, et al, Hardwood Academic Press.
Kemnitzer, Degradable Polymers derived from the Amino Acid L-Tyrosine, Handbook of Biodegradable Polymers, 1997, pp. 251-272, edited by Domb, et. al., Hardwood Academic Press.
Cohn and Younes, Biodegradable PEO/PLA, Journal of Biomaterials Research,1988, pp. 993-1009, vol. 22.

* cited by examiner

*Primary Examiner* — Michael G Hartley
*Assistant Examiner* — Jagadishwar Samala (57) ABSTRACT

An anti-adhesion sheet for placement upon the anterior wall of a vertebral body, wherein the sheet has a radius of curvature that is less than that of the anterior wall of the vertebral body.

4 Claims, 12 Drawing Sheets

ANTI-ADHESION SHEET

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

Surgery for the revision of an anterior lumbar motion disc, while rare, is particularly challenging due to adhesion that form following the mobilization of the great vessels during the initial procedure. The tenacity of these adhesions coupled with the fragility of the vena cava enhances the potential that this venous structure may become torn or ruptured during the revision surgery. Considering these factors and the technically demanding repair required, there is significant risk to the patient.

Anti-adhesion sheets have been proposed for use in both anterior motion disc implantation and anterior intervertebral fusion surgeries in order to maintain a dissection plain to the surgical site to reduce the tenacity, area and density of the adhesions. Historically, there have been many proposals for anti-adhesion devices for use in hernia repair and for the prevention of intra-abdominal adhesions. One such example of an anti-adhesion device for hernia repair is found in US Published Patent Application No. 2005/0192600. Such devices do not have to take into account the prevention of damage to great vessel walls. Anti-adhesion devices have also been used in the posterior region of the spine to prevent dural adhesions. These devices are typically described as being in the form of a gel, a thick plate or a mesh.

U.S. Pat. No. 6,869,938 ("Schwartz") discloses an anti-adhesion material that is available as either a membrane or gel, specifically comprising a polyacid, a polyalkylene oxide, and a water soluble multivalent cation.

U.S. Pat. No. 6,475,219 ("Shelokov") discloses an anti-adhesion barrier for use in spinal surgery, wherein the barrier has a pleat to allow stretching as a consequence of movement between vertebral bodies to which the barrier is connected. Shelokov further discloses that the anti-adhesion barrier may have a radiopaque tab to aid in locating the device once it is in a working position. Shelokov further discloses that the anti-adhesion barrier has a concave face having a radius of curvature equal to the radius of curvature of the vertebral body to which it is attached. See FIG. 1 of Shelokov. Shelokov further discloses that the anti-adhesion barrier has holes for receiving bone fasteners so that the device may be secured to the vertebral bodies.

SUMMARY OF THE INVENTION

It is an object of the present invention to provide an improved anti-adhesion barrier between the vessels and the spinal column, thereby inhibiting the formation of adhesions.

In one embodiment, the present invention relates to an anti-adhesion sheet that includes radiographic markers to help the surgeon visualize the device.

Therefore, in accordance with the present invention, there is provided an anti-adhesion sheet having an interior region and an edge region encompassing the interior region, and comprising at least one radiopaque marker, wherein the radiopaque marker defines the edge region of the sheet.

Also in accordance with the present invention, there is provided an anti-adhesion sheet having an interior region and an edge region encompassing the interior region, and comprising at least one radiopaque marker located at least partially in an interior region of the sheet.

Also in accordance with the present invention, there is provided a tab-less anti-adhesion sheet having a radiopaque marker.

Also in accordance with the present invention, there is provided an anti-adhesion sheet having a bulk region and a tab region, wherein the bulk region comprises a radiopaque marker.

In a second embodiment, the present invention relates to an anti-adhesion sheet that includes features for bony purchase to help the surgeon properly place the device.

Therefore, in accordance with the present invention, there is provided an anti-adhesion sheet having bony purchase features selected from the group consisting of mesh, adhesive and pre-attached bone anchors.

In a third embodiment, the present invention relates to an anti-adhesion sheet that includes a reduced radius of curvature to help the surgeon properly conform the device to the vertebral body surface and prevent migration.

Therefore, in accordance with the present invention, there is provided a method comprising:
  a) providing a vertebral body having an anterior wall defining a first radius of curvature,
  b) providing an anti-adhesion sheet having a concave face defining a second radius of curvature, wherein the first radius of curvature is greater than the second radius of curvature, and
  attaching the concave face of the anti-adhesion sheet to the anterior wall of the vertebral body.

DETAILED DESCRIPTION OF THE INVENTION

Figure 1A:
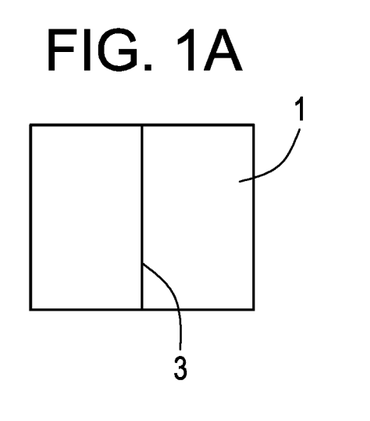
FIGS. 1a-1c disclose top views of anti-adhesions sheets having radiopaque markers therein.
Figure 1B:
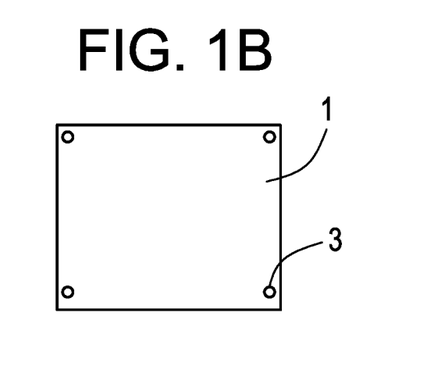
Figure 1C:
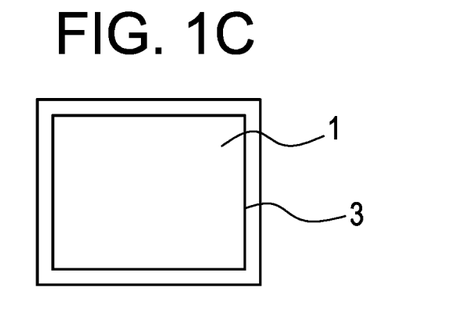

Now referring to FIGS. 1a-1c, in some embodiments, the present invention relates to an anti-adhesion sheet 1 that includes radiographic markers 3 to help the surgeon visualize the device. The sheet can comprise imaging markers that will make the sheet visible when viewed by a fluoroscope, MRI or CT. In preferred embodiments, the markings can be used to indicate midline (as in FIG. 1a), the corners of the sheet (as in FIG. 1b), or the edge or boundaries of the sheet (as in FIG. 1c).

For example, in some embodiments, the sheet has a plurality of corners, and the edge region includes a radiopaque marker located in each respective corner of the sheet In other embodiments, the radiopaque marker extends continuously along the edge region of the sheet.

Preferably, the radio-opacity of the sheet is created with a radiopaque material such as tungsten ink, barium sulfate, calcium sulfate, and metallic coatings.

In some embodiments, the sheet is dyed a particular color so that it is readily distinguishable when placed at the surgical site. This dye will make the sheet coverage apparent while enabling the surgeon to continue to see through the sheet and visualize the interbody device. Preferably, the dyed sheet remains translucent, so as to enable the surgeon to see through it as the surgeon closes. More preferably, the dyed sheet remains transparent.

In a second embodiment, the present invention relates to an anti-adhesion sheet that includes features for bony purchase to help the surgeon properly place the device.

Figure 2A:
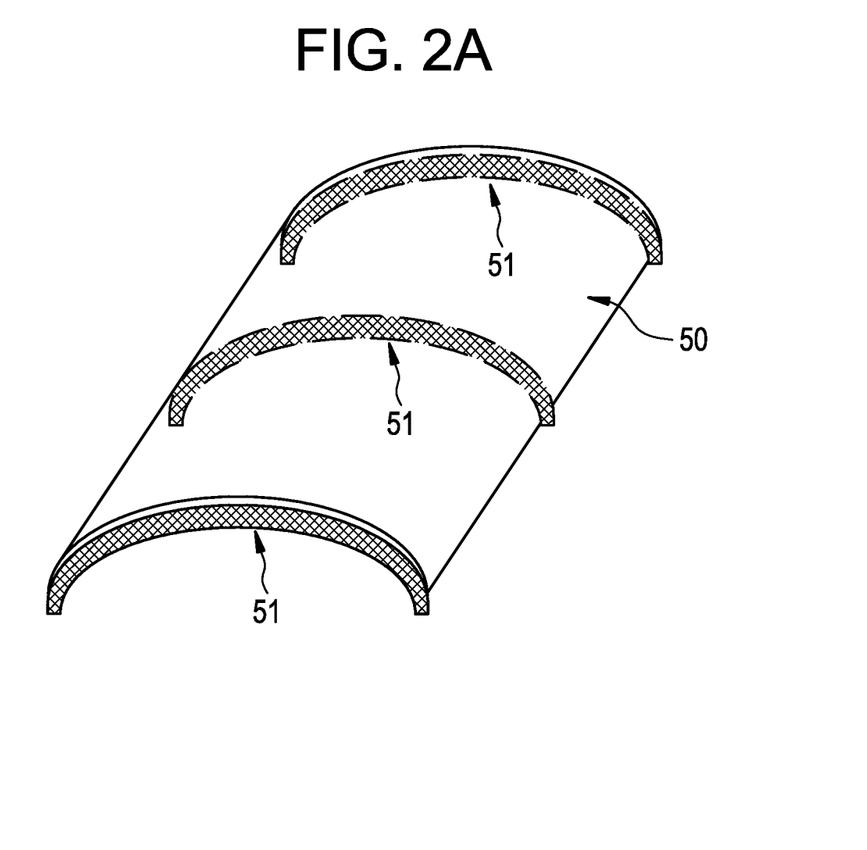
FIGS. 2a-b disclose perspective and side views of anti-adhesion sheets having mesh strips.
Figure 2B:
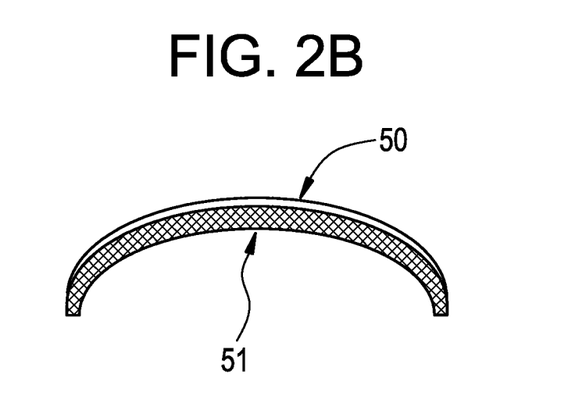

Now referring to FIG. 2a-b, in some embodiments, the anti-adhesion sheet 50 includes bony purchase features including mesh, such as mesh strips 51. These mesh strips allow for bony ingrowth and long term attachment. Preferably, the mesh strips are included on the concave side of the anti-adhesion sheet.

Figure 2C:
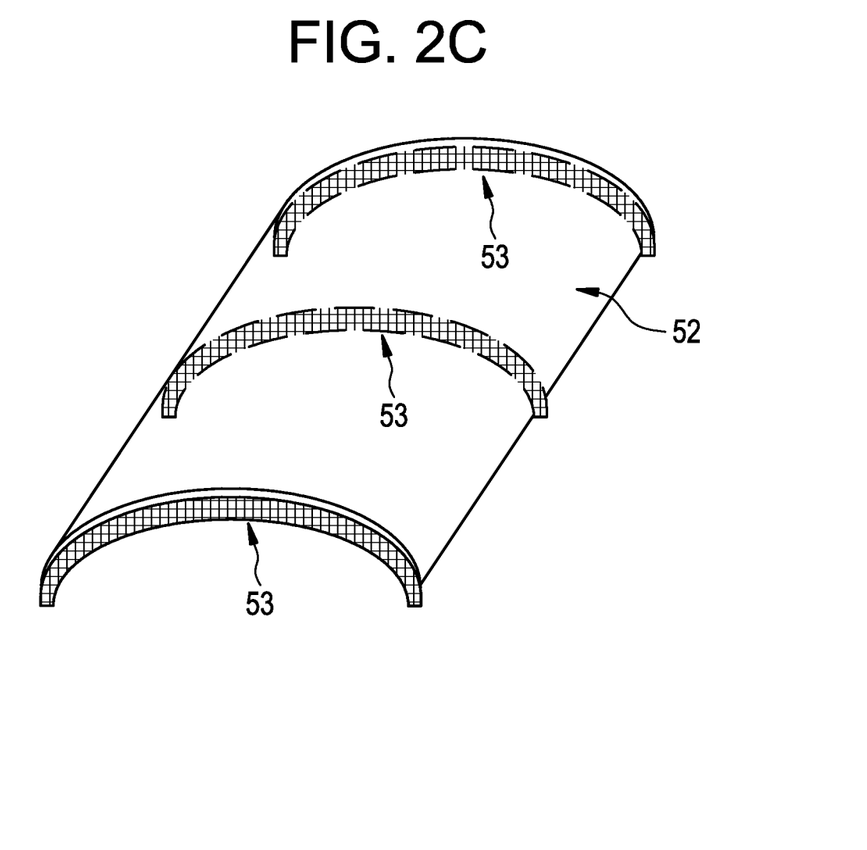
FIGS. 2c-d disclose perspective and side views of anti-adhesion sheets having adhesive strips.
Figure 2D:
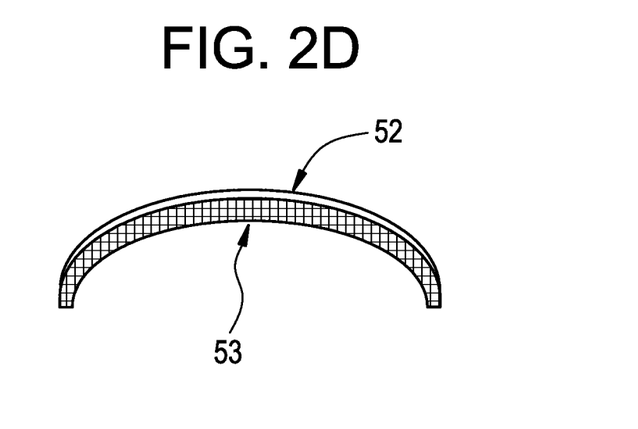

Now referring to FIG. 2c-d, in some embodiments, the anti-adhesion sheet 52 has bony purchase features including an adhesive strip 53, such as a surgical glue or a pressure sensitive adhesive strip. These features enhance attachment of the anti-adhesion sheet to the bony surface. In some embodiments, a surgical glue is selected, and is preferably selected from the group consisting of fibrin glue and the cyanoacrylate family of adhesives, including Closuer's surgical sealants. In some embodiments, the pressure sensitive adhesive is selected and is, for example, bone wax. Preferably, the adhesive is included on the concave side of the anti-adhesion sheet.

Figure 2E:
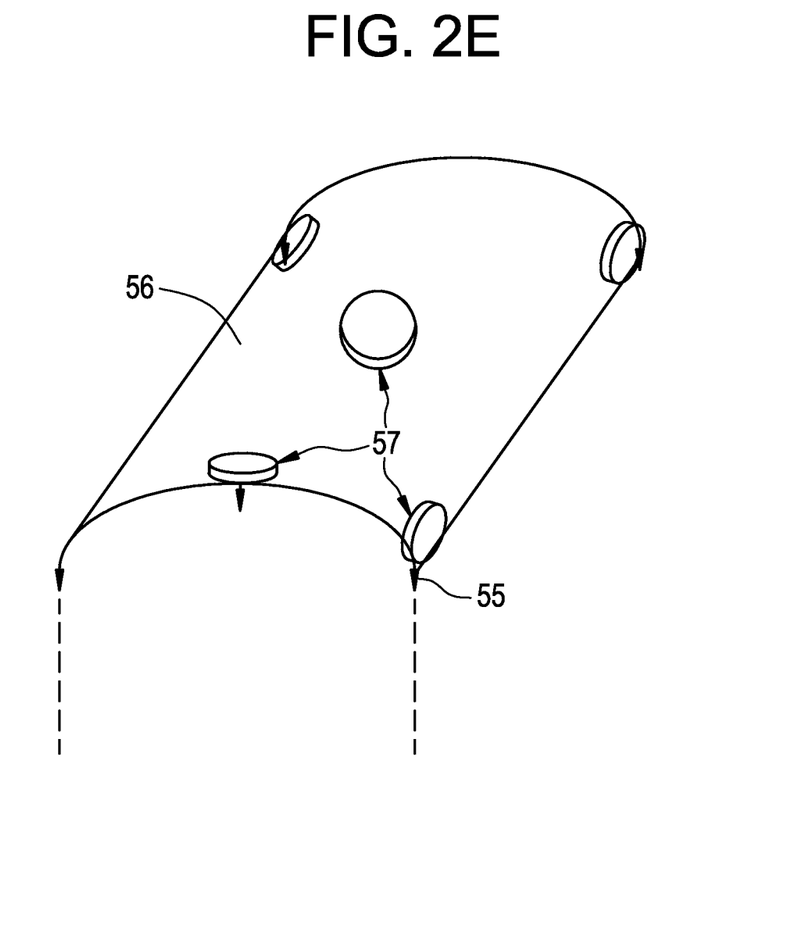
FIGS. 2e-f disclose perspective and side views of anti-adhesion sheets having pre-attached bone anchors.
Figure 2F:
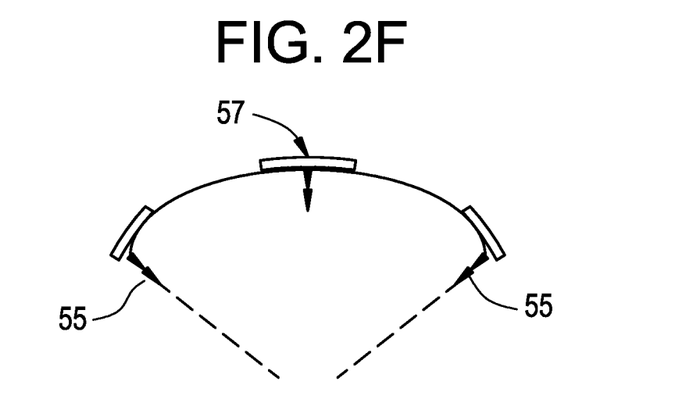

Now referring to FIG. 2e-f, in some embodiments, there is provided an anti-adhesion sheet 56 having bony purchase features including pre-attached bone anchors 55. The proximal ends of the bone anchors are attached to the anti-adhesion sheet in reinforced regions 57 of the anti-adhesion sheet. These reinforced regions add strength to the sheet so as to withstand the impact that occurs during attachment of the bone anchors to the vertebra. In some embodiments, the bone anchor are in-line attached as in FIG. 2e, while in others, the bone anchors are included angle attached as in FIG. 2f.

Figure 3A:
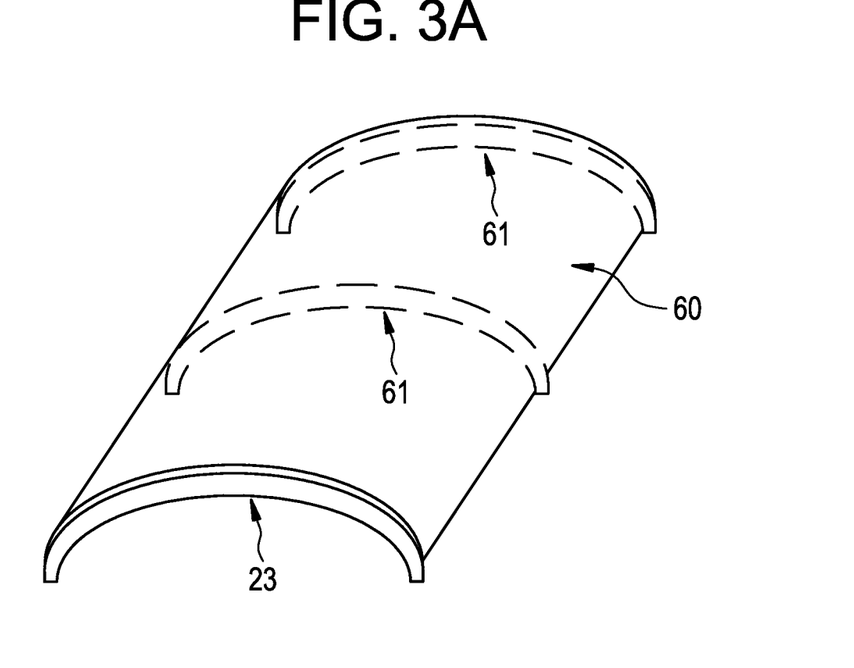
FIG. 3a-b discloses a perspective view of an anti-adhesion sheet having compression ridges.
Figure 3B:
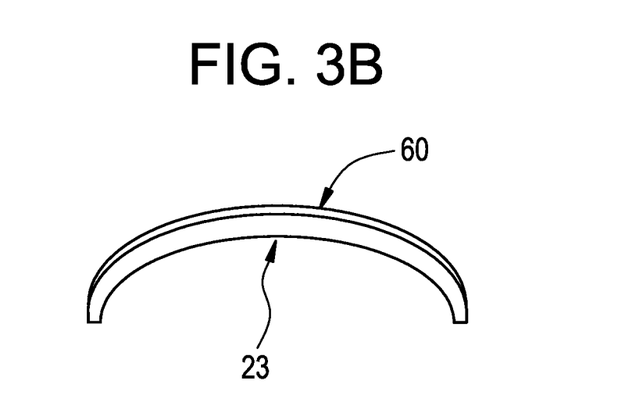

Now referring to FIG. 3a-b, there is provided an anti-adhesion sheet 60 having a plurality of compression ridges 61. The compression ridges enhance conformance and fit of the anti-adhesion sheet to the variations in the vertebral body surface. This will enable the sheet to attain the desired stiffness without having to increase the thickness of the entire sheet. It also enables the sheet to conform easily to the space while maintaining desirable handling characteristics.

Also in accordance with the present invention, there is provided an anti-adhesion sheet having a stiffness enhancement feature selected from the group consisting of a compression ridge and a rib.

In a third embodiment, the present invention relates to an anti-adhesion sheet that includes a reduced radius of curvature to help the surgeon properly conform the device to the vertebral body surface, prevent migration, and simplify placement and fixation of the sheet. In particular, the radius of curvature of the device is less than that of the anterior wall of the vertebral body upon which the device sits. As a result, when the sheet is pressed into place, the sheet deforms and the elastic nature of the sheet helps it to grab onto the vertebral column. The reduced radius ensures that the anti-adhesion sheet covers the tissue to be protected and maintains its position. The reduced radius also enhances deployment and handling of the anti-adhesion sheet.

Figure 4A:
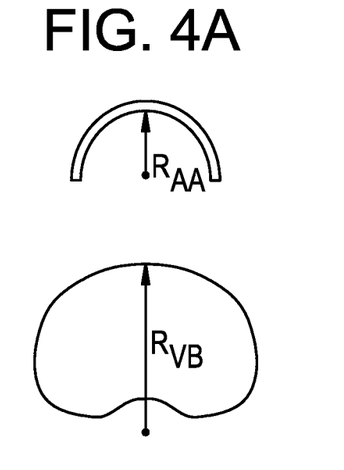
FIGS. 4a-4c disclose axial views of anti-adhesions sheets having a reduced radius of curvature being attached to the anterior wall of a vertebral body.

Now referring to FIG. 4a, there is provided an anti-adhesion sheet held in position above the anterior wall of a vertebral body, wherein the anti-adhesion sheet has a radius of curvature RAA that is less than the radius of curvature of the anterior wall of the vertebral body RVB.

Figure 4B:
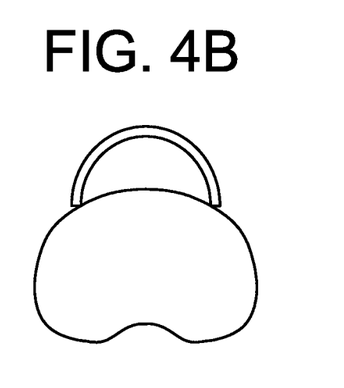

Now referring to FIG. 4b, upon initial placement of the device upon the vertebral body, the reduced radius allows insertion of the sheet with the sheet ends sliding along the vertebral body, preventing soft tissue manipulation and damage.

Figure 4C:
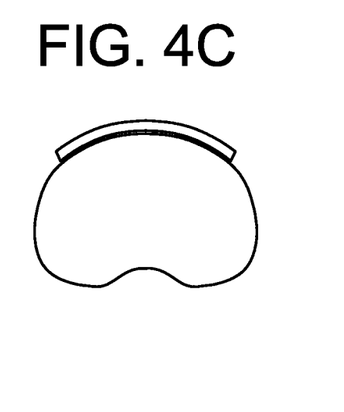

Now referring to FIG. 4c, the reduced radius further provides positive seating upon final placement as well as compressive force to hold it in place. Preferably, the device has a radius of curvature of between 0.5 cm and 5.0 cm.

The anti-adhesion device of the present invention is preferably provided in the form of a sheet having a thickness of between about 20 µm and about 400 µm.

Figure 5A:
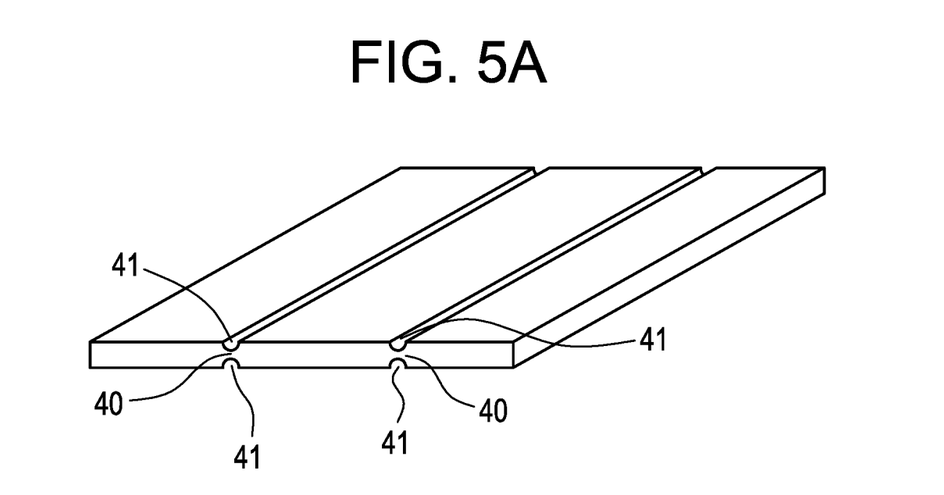
FIGS. 5a-b discloses perspective views of anti-adhesion sheets having bend zones.

The sheet may also incorporate bend zones. Now referring to FIG. 5a, the bend zones 40 are formed by opposing recesses 41 that produce areas of reduced wall thickness to facilitate bending or crimping at a specific location. For example, a benefit may be derived from providing a bend zone axially along several locations of the curvature and thereby allow the surgeon to improve conformance of the sheet to bony structure.

Therefore, in accordance with the present invention, there is provided an anti-adhesion sheet having a first face and a second face producing a first thickness therebetween, wherein the first face has a recess therein to produce a bend zone having a second wall thickness, wherein the first wall thickness is greater than the second wall thickness.

Figure 5B:
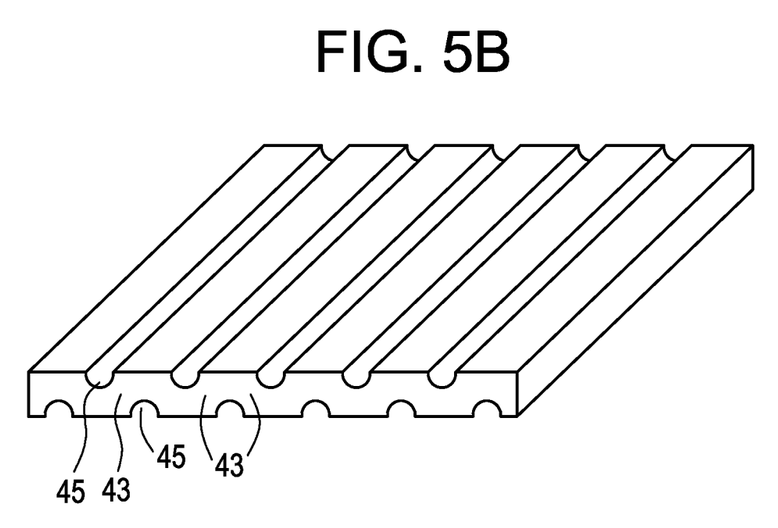

Now referring to FIG. 5b, the bend zones 43 are formed by offset recesses 45 that produce areas of reduced wall thickness to facilitate a more fine degree of bending or crimping at a specific location.

Figure 6A:
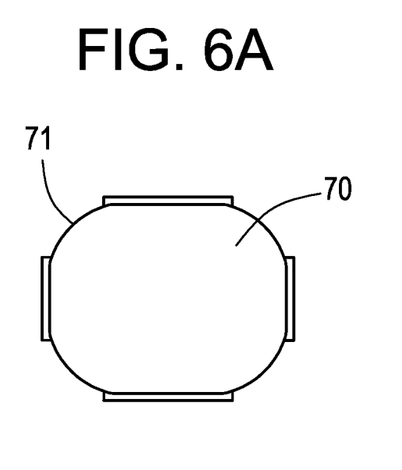
FIGS. 6a-b discloses top views of anti-adhesion sheets having rounded corners.
Figure 6B:
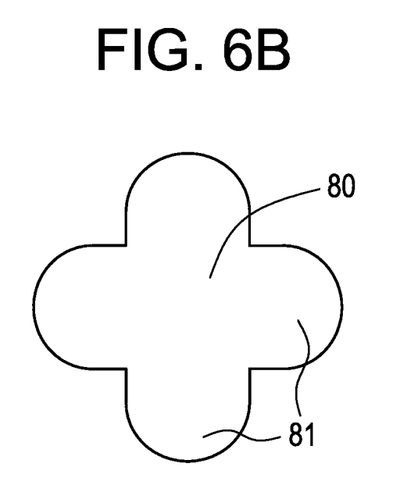

In order to increase the safety of the device in some embodiments, the anti-adhesion sheet 70 has rounded corners 71. Now referring to FIG. 6a, there is provided a square anti-adhesion sheet having rounded corners. Now referring to FIG. 6b, there is provided a square anti-adhesion sheet 80 having a cloverleaves 81.

The anti-adhesion sheet of the present invention can be either resorbable or permanent. Preferably, the anti-adhesion device is made from a material selected from the group consisting of polypropylene (non-resorbable) and polydioxanone (resorbable).

Some preferred materials of construction for the anti-adhesion sheet include fluoropolymers, coplymers of PVDF and HFP, silicones, PLA and PGA.

Preferred bioresorbable materials, which can be used to make the anti-adhesion sheets of the present invention, include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates). Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

Synthetic nonresorbable materials include silk, cotton, linen, nylon, polypropylene, polybutester, nylon and polyester.

A variety of bioabsorbable polymers can be used to make the anti-adhesion sheet of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.), polyurethanes, and blends thereof. For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\chi$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, $\chi,\chi$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Preferably, the bioresorbable material is selected from the group consisting of poly(lactic acid) ("PLA") and poly(glycolic acid)("PGA"), and copolymers thereof. In some of the preferred embodiments, one of the resorbable sutures is selected from the group consisting of PLA, PGA, polydioxanone (PDO), polycaprolactone (PCL), and mixtures thereof.

The anti-adhesion device of the present invention is preferably used in conjunction with anteriorly-placed interbody devices, such as motion discs and fusion cages.

One preferred method of attaching the adhesion reduction sheet to the anatomy is as follows:

First, following implantation of the interbody device, the surgeon manually places (or places with the help of instruments) the anti-adhesion sheet over the surgical site. At this time, the surgeon can cut the sheet to accommodate adjacent anatomy if necessary.

Once the anti-adhesion sheet is in place, the surgeon will place the distal end of the outer sleeve against the sheet. Now referring to FIG. 7, the outer sleeve 101 comprises:
  a) a tube 102 extending substantially through the entire length of the tool and forming an inner bore and an outer surface 103,
  b) a proximal end 105 comprising a hand grip 107,
  c) a notch 109 extending from the outer surface and located just distal of the handgrip (and used to illustrate orientation of the staple),
  d) a groove or slit 111 in the outer surface of the tube extending substantially through the entire length of the tool, and
  e) a distal end portion 113 having two prongs 115 extending axially therefrom and adapted to advance through the anti-adhesion sheet and enter the vertebral body (thereby preventing the instrument and sheet from slipping during placement of an attachment mechanism).

Next, an awl is used to make holes in the vertebral body for placement of the staple. Still referring to FIG. 7, the awl 121 comprises:
  a) an elongated shaft 122 having an outer surface 123 having a distal end portion 124,
  b) a proximal handle 125 having a polymeric impaction surface 127,
  c) a post 129 extending radially from the distal end portion of the outer surface of the shaft (and adapted to ride the groove of the outer sleeve during insertion in order to maintain the awl's orientation),
  d) a pair of prongs 131 extending axially from the distal end of the shaft and adapted to puncture cortical bone.

Figure 7:
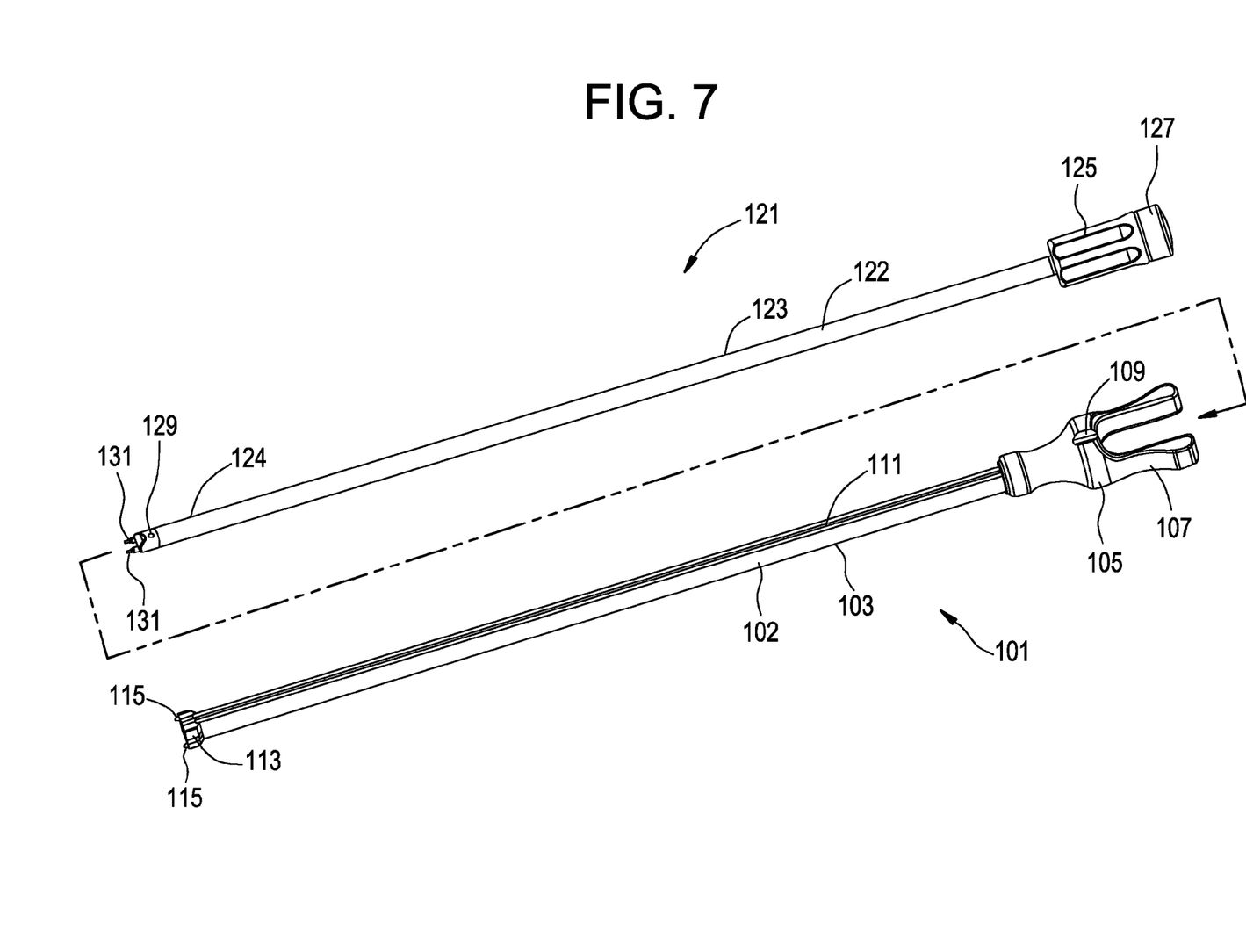
FIG. 7 discloses perspective views of an outer sleeve and an awl used to attach the present invention.

The awl is delivered down the tube of the outer sleeve and is proximally impacted to make holes in the vertebral body required for fixing the prongs of the attachment mechanism (here, depicted as a staple) in the vertebral body. Once the holes are made, the awl is carefully removed from the outer sleeve while maintaining the position of the outer sleeve.

Figure 8:
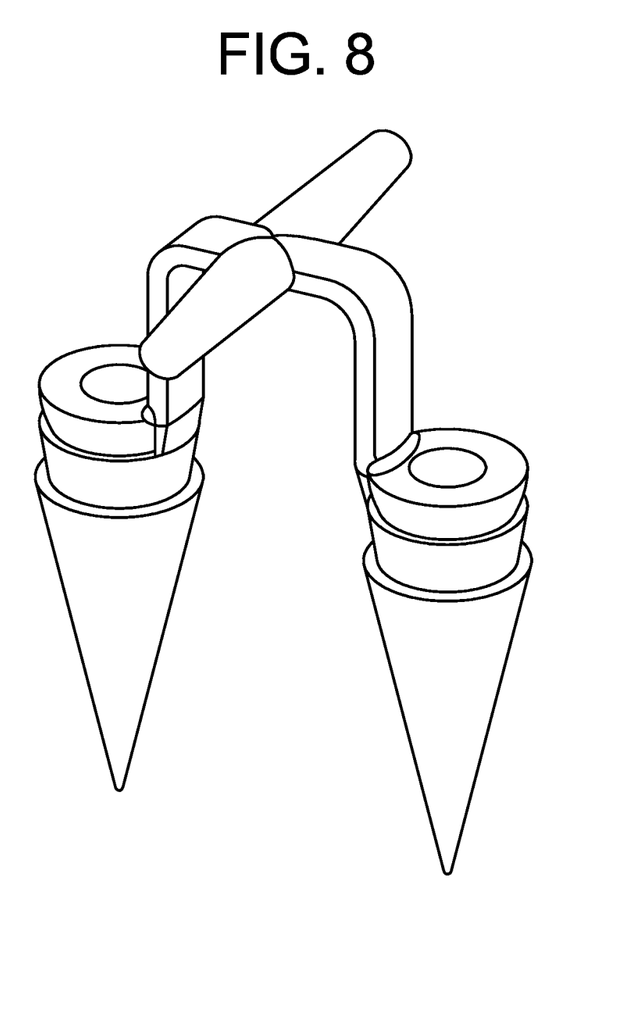
FIG. 8 is an embodiment of a staple used to attach the present invention to bony anatomy.

If a staple is selected as the attachment mechanism, then the Graft Fixation Device, available from DePuy Mitek of Raynham, Mass. may be used. One such staple is shown in FIG. 8. Similar staples made in accordance with U.S. Pat. Nos. 6,423,073; 6,436,110; 6,402,766; 6,179,840; 6,364,884; and 6,497,707, and US Published Patent Application Nos. 2002/0095157; 2002/0169465; 2002/0052628; and 2004/0138664 may be used as well.

Figures 9A, 9B:
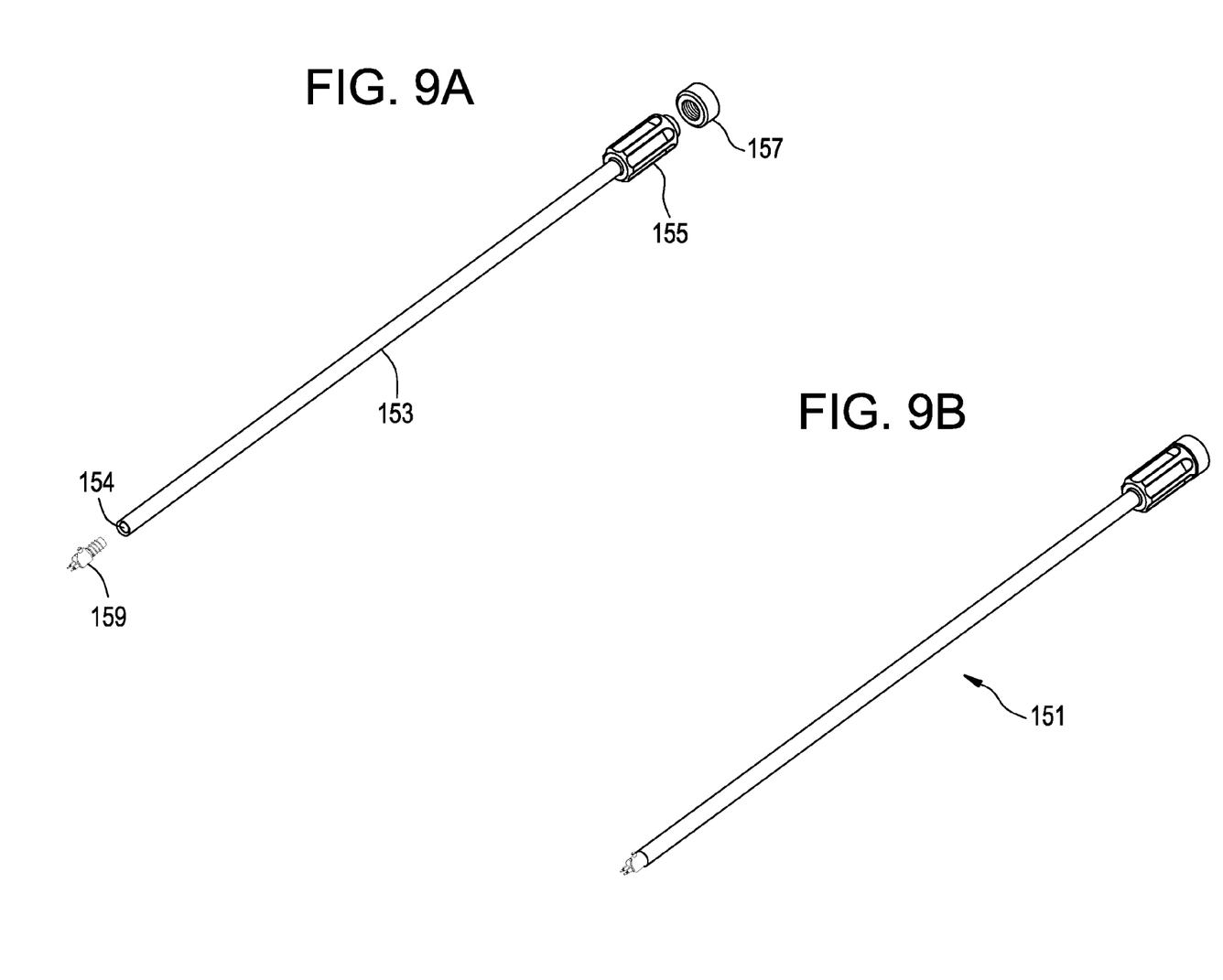
FIGS. 9a and 9b disclose exploded and assembled views of the inserter of the present invention.

After the appropriate staple is selected, it is loaded onto an inserter. In some embodiments, and now referring to FIGS. 9a and 9b, the inserter 151 includes:

a) an elongated shaft 153 having a threaded distal end 154,
b) a proximal handle 155 having a threadable endcap 157 adapted for impaction, and
c) a distal inserter tip 159.

Figure 10A:
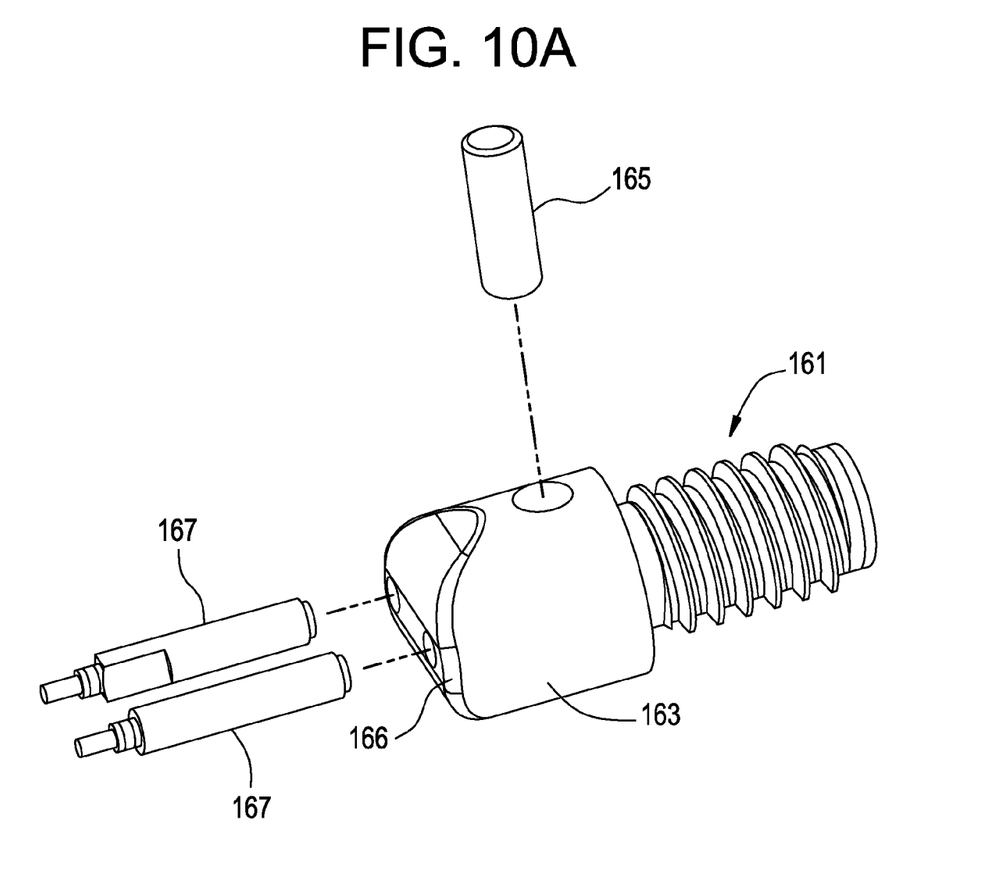
FIGS. 10a and 10b disclose exploded and assembled views of the inserter tip of the present invention.
Figure 10B:
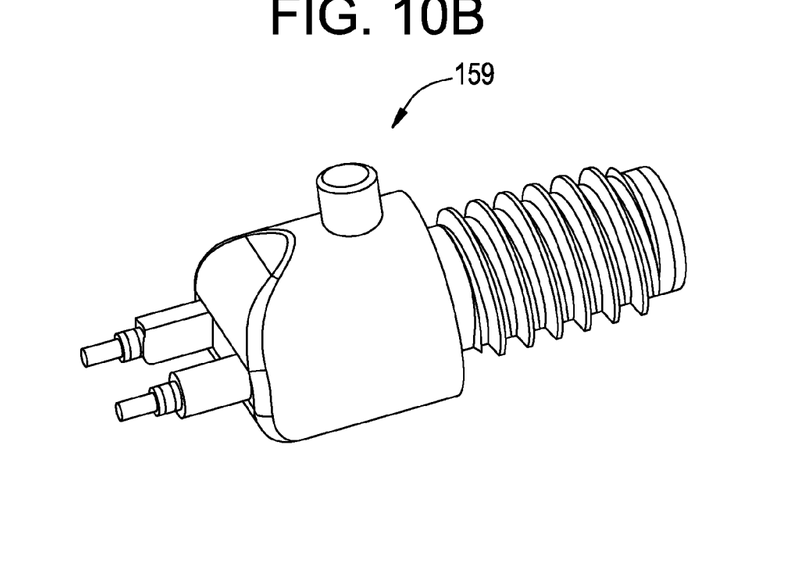

Now referring to FIG. 10*a* and 10*b*, in some embodiments, the distal inserter tip 159 has a) a threaded proximal end 161 for threadable reception on the threaded distal end of the shaft,
b) an intermediate section 163 having a radially extending orientation post 165, and
c) a distal end 166 having a pair of staple retention ports 167 extending axially therefrom.

Figures 11A, 11B:
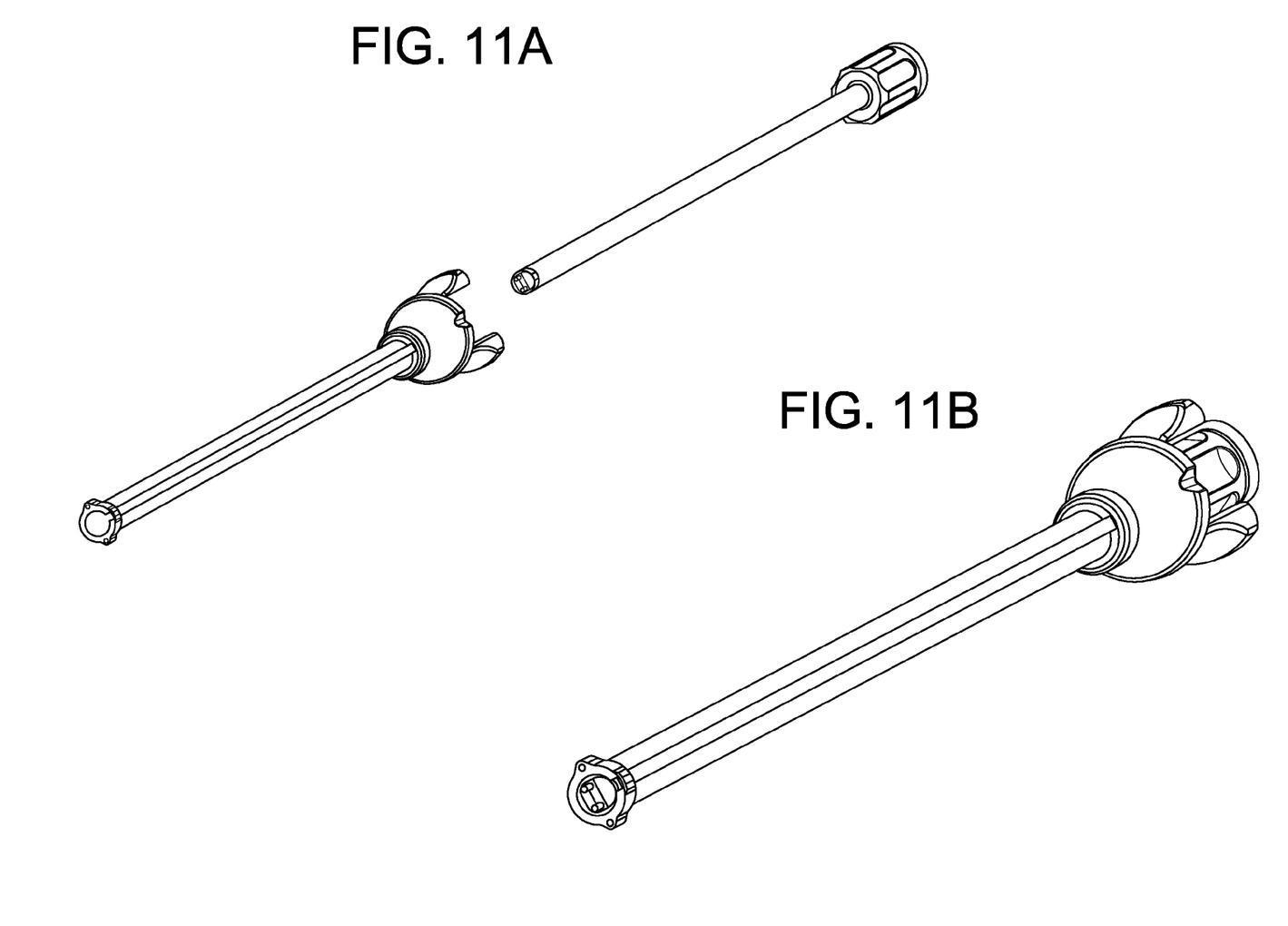
FIGS. 11a and 11b disclose aligned and assembled views of the inserter tip and outer sleeve of the present invention.

As shown in FIG. 11*a*, the inserter is passed through the barrel of the outer sleeve to form the assembly shown in FIG. 11*b*.

Next, impacted into place by impacting the proximal end of the inserter. Once the staple is completely seated, the entire instrument can be removed.

An awl is used in the above procedure because, in some embodiments, the attachment mechanism is a resorbable staple that may not have the structural strength necessary to puncture cortical bone. A resorbable attachment mechanism is typically used with a resorbable sheet. However, if a non-resorbable sheet is being used, a permanent attachment mechanism or staple may also be used. Selection of a permanent attachment mechanism or staple increases the number of materials that could be used for the attachment mechanism or staple. Stronger staple materials could eliminate the need for using the awl prior to staple placement.

We claim:

1. A single anti-adhesion sheet having the ability to inhibit the formation of adhesions between vessels and the spinal column when placed therebetween, the sheet having a first face and a second face producing a first thickness therebetween, wherein the first face has a recess therein to produce a bend zone having a second wall thickness, wherein the first wall thickness is greater than the second wall thickness, the sheet has bony purchase features like adhesive and pre-attached bone anchors, the sheet further having a radius of curvature to prevent migration and simplify placement and fixation of sheet, wherein the bend zone is provided axially along several locations of the curvature, and wherein a strip selected from the group consisting of a mesh strip and an adhesive strip is included on a concave surface of the anti-adhesion sheet.

2. The anti-adhesion sheet of claim 1, wherein the recess is a groove.

3. The anti-adhesion sheet of claim 1 wherein the first face has a plurality of substantially parallel grooves therein to produce a plurality of bend zones, each bend zone having the second wall thickness.

4. The anti-adhesion sheet of claim 1 having a radius of curvature of between 0.5 cm and 5.0 cm.

* * * * *